United States Patent [19]

Kaneko

[11] Patent Number: 5,396,347
[45] Date of Patent: Mar. 7, 1995

[54] APPARATUS FOR SYNTHESIZING A MEDICAL IMAGE AND CORRESPONDING NUMERICAL DATA AND RECORDING THE SYNTHESIZED IMAGE

[75] Inventor: Makoto Kaneko, Ootawara, Japan
[73] Assignee: Kabushiki Kaisha Toshiba, Kawasaki, Japan
[21] Appl. No.: 190,579
[22] Filed: Feb. 2, 1994

Related U.S. Application Data

[63] Continuation of Ser. No. 709,276, Jun. 3, 1991, abandoned.

[30] Foreign Application Priority Data

Jun. 4, 1990 [JP] Japan ................................ 2-144445

[51] Int. Cl.⁶ .............................................. H04N 1/40
[52] U.S. Cl. .......................................... 358/448; 382/6
[58] Field of Search ................... 348/162, 163, 164; 378/8, 23, 95, 19, 98, 99, 100; 364/413, 22, 413.14, 413.03, 413.04, 413.05, 413.19, 413.23; 382/6, 56; 358/261.4, 262.1, 262.2, 426, 430, 432; 250/486.1

[56] References Cited

U.S. PATENT DOCUMENTS

| | | | |
|---|---|---|---|
| 4,641,328 | 2/1987 | Fujise | 378/95 |
| 4,642,621 | 2/1987 | Nemoto et al. | 364/413.22 |
| 4,700,299 | 10/1987 | Kimura et al. | 364/413.22 |
| 4,719,508 | 1/1988 | Sasaki et al. | 358/98 |
| 4,768,083 | 8/1988 | Romesburg | 358/22 PIP |
| 4,768,099 | 8/1988 | Mukai | 358/426 |
| 4,833,625 | 5/1989 | Fisher et al. | 364/413.22 |
| 5,031,036 | 9/1991 | Kikuchi et al. | 358/98 |
| 5,077,769 | 12/1991 | Franciose | 378/99 |
| 5,111,306 | 5/1992 | Kanno et al. | 358/403 |
| 5,151,795 | 9/1992 | Adachi | 382/6 |

FOREIGN PATENT DOCUMENTS

| | | | |
|---|---|---|---|
| 2257772 | 5/1974 | Germany | 378/99 |
| 3325939A | 9/1984 | Germany | |

Primary Examiner—Stephen Brinich
Assistant Examiner—Jerome Grant, II
Attorney, Agent, or Firm—Finnegan, Henderson, Farabow, Garrett & Dunner

[57] ABSTRACT

An output of a TV camera for picking up an X-ray fluoroscopic image is supplied to an image memory. An output of an electrocardiograph is supplied to a cardiograph memory. The output from the image memory is subjected to subtraction processing to obtain an angiogram and the angiogram data is supplied to an image synthesizing circuit. The image synthesizing circuit reads out data of the latest several seconds from the cardiograph memory, and produces a cardiogram on the basis of the read-out data. A synthesis image, in which the cardiogram is superimposed on part of the angiogram, is displayed on a display. The outputs from the image memory and the cardiograph memory are supplied to a recording/reproducing processor. The image data is compressed, and both the compressed image data of one field and the cardiograph output data representing the cardiogram superimposed on the field image are recorded on a recording area of one filed image of a video tape. The data reproduced from the video tape is separated into image data and cardiograph output data at every field by the recording/reproducing processor. The image data is data-expanded and supplied to the image memory, and the cardiograph output data is supplied to the cardiograph memory.

9 Claims, 2 Drawing Sheets

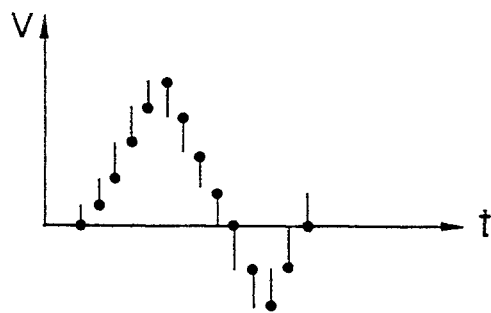
F I G. 2
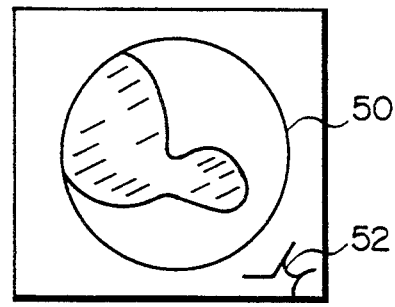
F I G. 3
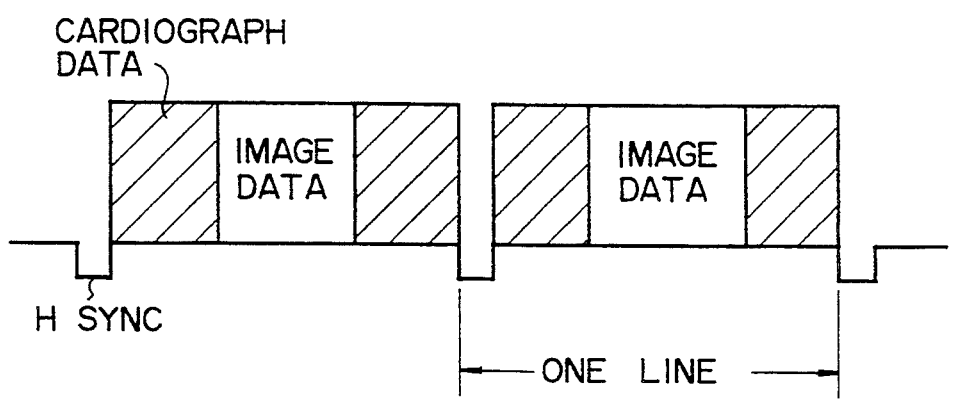
F I G. 4
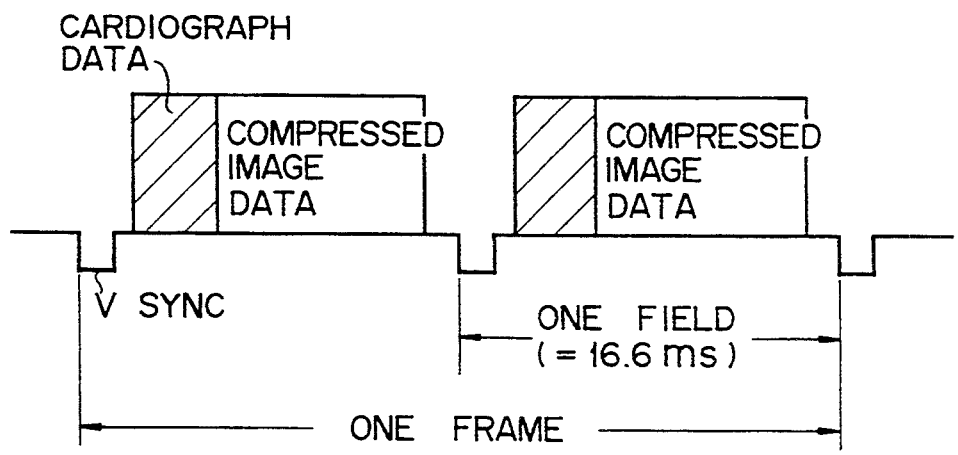
F I G. 5

APPARATUS FOR SYNTHESIZING A MEDICAL IMAGE AND CORRESPONDING NUMERICAL DATA AND RECORDING THE SYNTHESIZED IMAGE

This application is a continuation of application Ser. No. 07/709,276, filed Jun. 3, 1991, now abandoned.

BACKGROUND OF THE INVENTION

1. Field of the Invention

The present invention relates generally to an image processing apparatus, and more particularly to an image processing apparatus for recording and reproducing a synthesis image formed by superimposing, on part of image data supplied from the outside, attribute data which is also supplied from the outside and associated with the image data.

2. Description of the Related Art

This type of apparatus is widely used in the field of techniques relating to medical imaging or diagnosis. For example, in many cases, an angiogram obtained by a digital fluorography (DF) apparatus used as a diagnosing X-ray apparatus is displayed on a display device such as a TV monitor, and simultaneously a cardiogram spanning a time period from a predetermined time point to the time point of the display of the present angiogram is displayed. The view field of the X-ray fluoroscopic image is regularly circular, since the view field of the output optical image of an image intensifier tube is circular. Since the corners of the screen showing the angiogram are non-effective areas, the cardiogram may be superimposed anywhere in the corners without preventing the display of the angiogram. Thus, the synthesis image containing both the cardiogram (attribute data) and angiogram (image data) can be displayed. The angiogram obtained by the DF apparatus can be displayed in real time; however, the cardiogram cannot. The cardiogram indicates an output (cardio-potential) from an electrocardiograph over a time period between a time point at which the present angiogram is produced and a time point preceding this time point by several seconds. Thus, the output (attribute data) of the electrocardiograph is stored in a buffer memory, and a portion of the cardio-potential data corresponding to a time period associated with the angiogram obtained by the DF apparatus is read out from the buffer memory and superimposed on the angiogram. Thereby, a cardiogram is produced.

A conventional method of recording image data and attribute data relating to the above-described synthesis image will now be described. Image data from the DF apparatus are supplied to the display device and also to a recording device such as a digital VCR (video cassette recorder) and recorded successively on a video tape at every frame (more exactly, at every field). In this case, the output from the electrocardiograph has not yet been supplied to the VCR and is stored in the buffer memory. After a single diagnosing operation is completed and recording of all images is completed, all cardio-potential data associated with the single diagnosing operation are read out from the buffer memory and recorded, as a unit, next to the image data recording area of the tape. In the case of reproduction, similarly, all angiogram image data associated with the single diagnosing operation are reproduced and stored in the image memory. Thereafter, all cardio-potential data are reproduced and stored in the buffer memory. Then, the angiogram is read out from the image memory and the cardio-potential data, which spans a time period from a time point at which the angiogram is produced to a time point preceding this time point by several seconds, are read out. The cardiogram formed on the basis of the read-out data is superimposed on a corner of the angiogram.

In the prior art described above, the image data and cardio-potential data are recorded at different places on a video tape at different time points. Thus, a time is wasted in recording the cardio-potential data, after the image data has been recorded. Despite the fact that both angiogram and cardio-potential data are simultaneously produced, these cannot be recorded simultaneously. In addition, in the case of reproduction, it is necessary to read out all angiogram data at first and then read out cardio-potential data, in order to form a synthesis image in which the cardiogram is superimposed on the angiogram. That is, the synthesis image cannot be reproduced and displayed immediately. All image data and all cardio-potential data must be reproduced even if only one synthesis image needs to be reproduced. Thus, the efficiency of the operation of the apparatus is not good.

SUMMARY OF THE INVENTION

The present invention has been made in consideration of the above circumstances, and its object is to provide an image processing apparatus capable of recording, almost simultaneously, image data and attribute data associated with the image data and superimposed on the image data and displayed, both of which data are produced almost simultaneously, and capable of reproducing and displaying both data almost simultaneously in a reproducing mode, thereby reducing recording and reproducing time.

In order to achieve this object, there is provided an image processing apparatus comprising:

display means for synthesizing externally supplied image data and externally supplied attribute data relating to the image data and displaying a synthesis data;

recording means for recording the image data and the attribute data, displayed by the display means, on one image recording area of an image recording medium; and reproducing means for reproducing data from said one image recording area of the image recording medium, dividing the reproduced data into image data and attribute data, and supplying both data to the display means.

According to the image processing apparatus of this invention, one unit of image data and associated attribute data which are synthesized and displayed by the display means are recorded on one unit of image recording area of the recording medium. Thus, the image and the attribute data which are produced almost simultaneously can be recorded almost simultaneously. In the reproducing mode, too, both data can be reproduced and displayed almost simultaneously, thereby reducing the recording and reproducing time.

Additional objects and advantages of the present invention will be set forth in the description which follows, and in part will be obvious from the description, or may be learned by practice of the present invention. The objects and advantages of the present invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the present invention and, together with the general description given above and the detailed description of the preferred embodiments given below, serve to explain the principles of the present invention in which:

FIG. 2 shows an example of a cardiogram obtained in the embodiment;

FIG. 3 shows an example of a display synthesis image in the embodiment;

FIG. 4 shows an example of a signal format recorded in a digital VCR serving as a recording device in the embodiment; and FIG. 5 shows another example of the signal format recorded in the digital VCR serving as recording device in the embodiment.

DETAILED DESCRIPTION OF THE PREFERRED EMBODIMENTS

Figure 1:
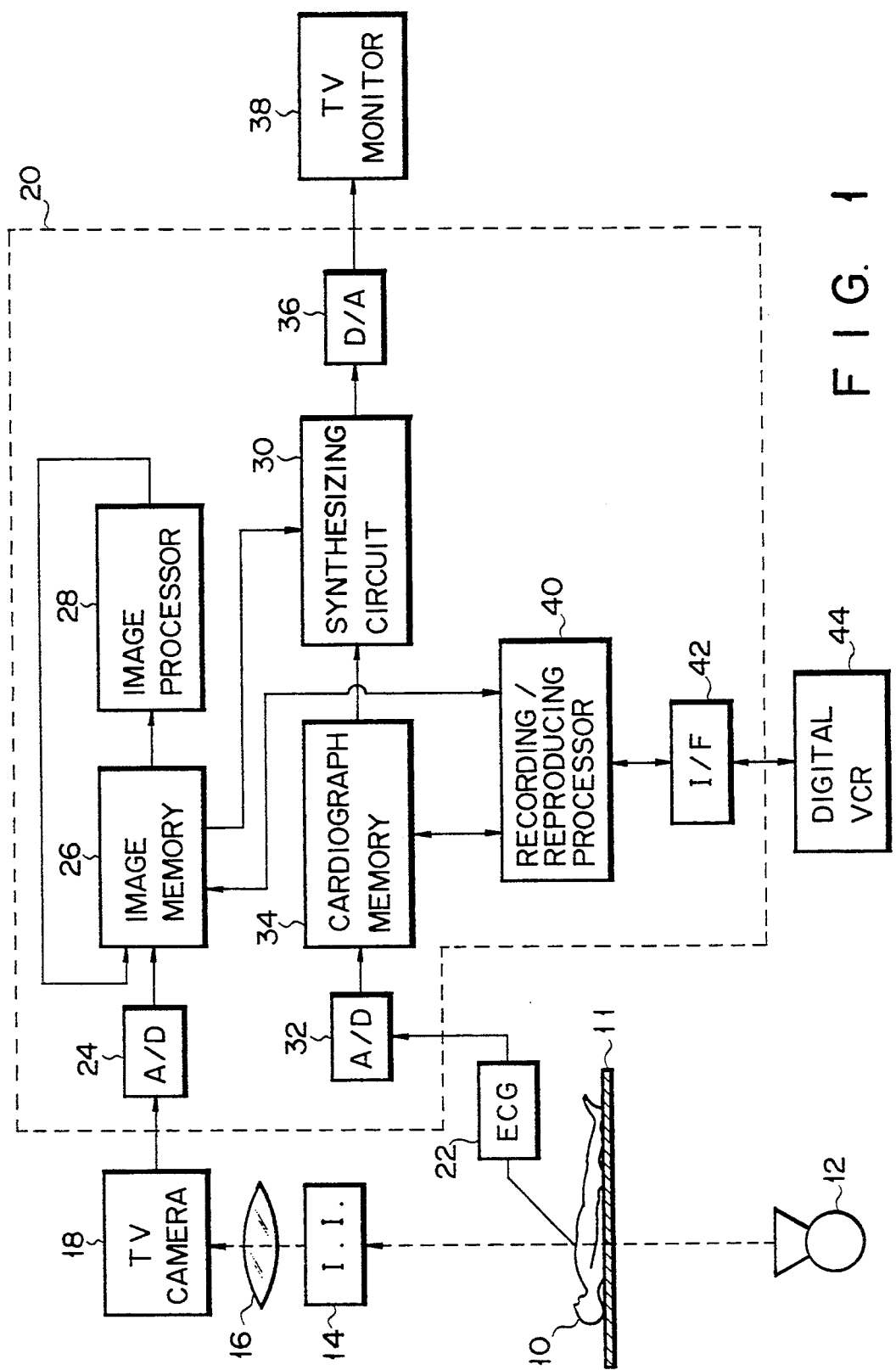
FIG. 1 is a block diagram showing an image processing apparatus according to an embodiment of the present invention.

An embodiment of the image processing apparatus of the present invention will now be described with reference to the accompanying drawings. FIG. 1 is a block diagram showing a structure of the embodiment of the invention as applied to a DF apparatus. A bed 11 is provided on a DF apparatus body (not shown). An X-ray tube 12 is situated below the bed 11. The X-ray tube 12 emits X-rays to a subject 10 on the bed 11. The X-rays, which have passed through the subject 10, are input to an image intensifier tube 14 provided above the bed 11 and the input X-rays are converted to an optical image representing the X-ray transmittance image of the subject 10. The optical image output from the image intensifier tube 14 is input to a monochromatic TV camera 18 through an optical system 16. The view field of the optical image output from the image intensifier tube 14 is circular. The output from the TV camera 18 is supplied to an image processing device 20. On the basis of the optical image, the TV camera 18 produces an X-ray image of the subject 10. The subject 10 is connected to an electrocardiograph 22 for detecting a cardio-potential. The output from the electrocardiograph 22 is also supplied to the image processing device 20 as an attribute data of the X-ray image. The TV camera 18 may comprise an image-pickup tube or a solid image-pickup device such as a charge-coupled device (CCD).

The X-ray image data output from the TV camera 18 is fed to an image memory 26 through an A/D converter 24 and is stored therein temporarily. The TV camera 18 outputs interlaced frame images at a rate of 30 frames per second (i.e. 60 field images per second). The image memory 26 has such a capacity as to store X-ray image data of several frames. The image data in the image memory 26 is fed to an image processor 28 and subjected to various image processing. The processed image data are stored in the image memory 26 in an updating manner. The image processor 28 calculates a subtraction image between two continuous frame images. Thus, on the basis of the subtraction between the two images obtained before and after a contrast medium reaches the artery of a region-of-interest (ROI) of the subject 10 after the medium is injected in the vein, a high-contrast angiogram image from which an image of the regions other than the blood vessel has been removed can be obtained. In addition, the image processor 28 reduces noise by means of a recursive filter, emphasizes an edge by means of a spatial filter, and carries out window processing for adjusting a display gray level. The image data in the image memory 26 subjected to such image processing is fed to a synthesizing circuit 30.

A cardio-potential data output from the electrocardiograph 22 is supplied to a cardiograph memory 34 through an A/D converter 32, and is temporarily stored in the memory 34. The cardio-potential data is output at a cycle of, for example, 240 Hz. The cardiograph memory 34 has such a capacity as to store the data output from the electrocardiograph 22 over several seconds (about 2 to 3 seconds) which is necessary for producing a cardiogram. The output from the cardiograph memory 34 is input to the synthesizing circuit 30. The synthesizing circuit 30 has a first frame memory for producing a cardiogram from the cardio-potential data and a second frame memory for synthesizing the angiogram and the cardiogram and displaying a synthesis image. As is shown in FIG. 2, coordinates (ordinate=cardio-potential level v: abscissa=time t) is imaginarily set in the first frame memory. The output data from the cardiograph memory 34 is plotted in the coordinates. In order to connect all plotted data, a vertical bar is drawn from each plotted point to the level of the next point. Thus, a cardiogram is produced. In this case, it is supposed that the output cycle of the electrocardiograph is equal to the horizontal resolution of a display. Thus, the vertical bars are drawn. If the horizontal resolution is higher than the output cycle of the electrocardiograph, the cardiogram may be produced by drawing vertical bars after interpolating data along the time axis, or plotting only the points after interpolating data along the time axis in units of resolution. As is shown in FIG. 3, the second frame memory for display of the synthesizing circuit 30 stores data relating to a cardiogram 52 and a angiogram 50. The angiogram 50 of a circular view field is displayed at the center of the display screen and the cardiogram 52 is displayed at a non-effective area of the screen, i.e. a corner of the screen. The output (data of the second frame memory) of the synthesizing circuit 30 is supplied to a display device (TV monitor) 38 via a D/A converter 36.

On the other hand, the image memory 26 and cardiograph memory 34 are connected to a digital VCR 44 via a recording/reproducing processor 40 and an interface 42. The recording/reproducing processor 40 superimposes cardio-potential data (attribute data) on a portion of the output data (image data) of the image memory 26, which is other than the effective image area, thereby recording, on a single image recording area (one field image area, in this case) of a video tape, both image data and attribute data relating to the synthesis image displayed on the TV monitor 38. Specifically, the effective image area of the angiogram is only within the circular view field, and the cardio-potential data can be superimposed on the region other than the effective image area of the angiogram. As is shown in FIG. 4, the effective image area of each line image data is only its center portion; thus, even if cardio-potential data is recorded at the peripheral portion of the line image data, the angiogram cannot be adversely affected. The portions of the effective image areas of the respective line image data vary from one another. Thus, the time periods in which cardio-potential data can be superimposed on each line image data differ from one another. If the control of superimposing is troublesome or the non-effective image area is smaller than the cardio-potential data, it is possible that the image data is compressed and the capacity of a single image data is made smaller than a single image recording area of the recording medium and the cardio-potential data is stored in the remaining portion. For example, as shown in FIG. 5, it is possible that the compressed image data of one field is assigned to the latter part of each field period (16.6 ms) and the cardio-potential data is assigned to the former part of the field period. Though not shown, the order of recording the cardio-potential data and the image data may be reversed, and one cardiogram data may be assigned to one of two fields forming a frame.

In the case of reproduction, a data read out from the VCR 44 is similarly divided into an image data and a cardio-potential data in the recording/reproducing processor 40, and the divided components are supplied to the image memory 26 and the cardiograph memory 34, respectively. When the image data is data-compressed and stored, the reproduced image data is data-expanded and fed to the image memory 26. Thus, in the reproducing mode, each field image is stored in the image memory 26 and cardio-potential data corresponding to the cardiogram assigned to the field image is stored in the cardiograph memory 34.

The operation of the embodiment having the above structure will now be described. A contrast medium is injected to the vein of the subject 10, and X-rays are radiated on the subject 10. Each frame X-ray fluoroscopic image data output from the TV camera 18 is successively written in the image memory 26 via the A/D converter 24. Simultaneously, the output from the cardiograph 22 indicating the cardio-potential of the subject 10 is successively written in the cardiograph memory 34 through the A/D converter 32. Each frame image data in the image memory 26 and the image data of the next frame are subjected to a subtraction processing. Thus, on the basis of frame images obtained before and after the contrast medium reaches the artery of the region-of-interest (ROI), an angiogram from which the image other than the image of the blood vessel has been removed can be obtained. The angiogram of each frame is supplied to the synthesizing circuit 30. The synthesizing circuit 30 reads out, from the cardiograph memory 34, the cardio-potential data obtained until about two seconds before the time point corresponding to the angiogram frame. Based on the read-out data, the cardiogram waveform as shown in FIG. 2 is superimposed on the area other than the circular effective image area of the angiogram, and the resultant image is displayed on the TV monitor 38.

On the other hand, the data relating to the angiogram and cardiogram displayed on the TV monitor 38 is supplied from the image memory 26 and cardiograph memory 34 to the recording/reproducing processor 40. As has been described above, the recording/reproducing processor 40 functions, as shown in FIGS. 4 and 5, to record the synthesis image data formed of the angiogram and cardiogram and displayed on the TV monitor 38 on the image recording area of a single field of the video tape. Thus, it is possible to simultaneously record the angiogram and cardiogram data on the VCR 44 which are simultaneously displayed.

In the reproducing mode, similarly, the recording/reproducing processor 40 divides the data read out from the VCR 44 into the image data and cardio-potential data at every field. The image data and cardio-potential data are written in the image memory 26 and the cardiogram memory 34, respectively. Thus, only by reproducing the data on the image recording area of one field of the video tape, the data relating to the angiogram and the corresponding cardiogram can simultaneously be reproduced and a synthesis image in which the cardiogram is superimposed on the angiogram can be immediately displayed.

As has been described above, according to the present invention, there is provided an image processing apparatus wherein the synthesis image formed of the image data and the related attribute data displayed by the display means is recorded on a single image recording area of a recording medium. Thus, the image data and attribute data, both of which are produced almost simultaneously, can be recorded almost in real time. In the reproducing mode, too, both data can be reproduced and displayed almost simultaneously and the recording/reproducing time can be shortened. The recording format for the image data and attribute data may be a format wherein attribute data is assigned to a non-effective data area of image data, or a format wherein image data is compressed and both the compressed image data and attribute data are assigned to the image recording areas of each field or frame of the recording medium. Unlike in the prior art, the time taken for recording attribute data after image date has been recorded can be saved, and therefore the recording time can be reduced. In addition, in the reproducing mode, unlike in the prior art, it is not necessary to read all image data in advance. Only by reproducing a data of a desired one frame, the image and related attribute data can be reproduced, as a synthesis image, simultaneously and immediately. Thereby, the through-put can be increased and the operator's work load can be reduced.

Additional advantages and modifications will readily occur to those skilled in the art. Therefore, the present invention in its broader aspects is not limited to the specific details, representative devices, and illustrated examples shown and described herein. Accordingly, various modifications may be made without departing from the spirit or scope of the general inventive concept as defined by the appended claims and their equivalents. For example, the attribute data to be recorded simultaneously with the image is not limited to data relating to a living body and may be general data associated with the image. In the case of the data relating to a living body, this data is not limited to the cardiogram, but may be a blood pressure waveform or a spirogram. The living body data may not be displayed as a waveform, and it may be displayed as a table or simple numerical values. In the above description, the image data is an angiogram obtained from an X-ray fluoroscopic image; however, the image data is not limited to this and may be ultrasonic image data obtained by an ultrasonic fluoroscopic apparatus, image data obtained by an endoscope, or image data obtained by a nuclear medicine imaging apparatus. In the case of the X-ray fluoroscopic image, this image is not limited to a angiogram obtained after image processing such as subtraction processing or filtering, and may be an X-ray fluoroscopic image before the processing. In the above embodiment, since the TV camera picks up images in an interlace system, the image data is compressed such that cardio-potential data is assigned prior to compressed image data at each field image; however, in the case of a non-interface system, the image data and attribute data may be recorded at each frame. In addition, the attribute data may not be recorded before and after the compressed image data; the attribute data may be assigned within the image data. The recording means is not limited to a digital VCR, but may be an analog VCR. Furthermore, the recording means is not limited to VCRs, but may be a recording device using a recording medium such as a disc, or a recording device such as a semiconductor memory. In the above embodiment, reproduced data is supplied to the synthesizing circuit 30 after it was once stored in the image memory 26 and cardiograph memory 34; however, it may be supplied directly to the synthesizing circuit 30.

What is claimed is:

1. An X-ray diagnosing apparatus comprising:
   X-ray fluoroscopic means for radiating x-rays on a subject, converting the X-rays which have passed through the subject into an optical image, and picking up the optical image, thereby obtaining fluoroscopic X-ray image data;
   detecting means for detecting living body data of the subject;
   storage means for storing said living body data over a time period between a second time, at which the fluoroscopic X-ray image data output from said X-ray fluoroscopic means is obtained, and a first time, preceding the second time by a predetermined length of time;
   display means for displaying a main image including a fluoroscopic X-ray image corresponding to the optical image based on the fluoroscopic X-ray image data output from said X-ray fluoroscopic means, and displaying a secondary image based on the living body data stored in said storage means by superimposing the secondary image on an area of the main image which does not include the fluoroscopic X-ray image of the subject; and
   recording means for recording the fluoroscopic X-ray image data output from said X-ray fluoroscopic means corresponding to the main image displayed by said display means and the living body data stored in said storage means, on a single image recording area of a video recording medium, whereby individual pieces of the fluoroscopic X-ray data and the living body data remain distinct.

2. The apparatus according to claim 1, wherein said detecting means is an electrocardiograph, and said main image and secondary image displayed by said display means are an angiogram and a cardiogram.

3. The apparatus according to claim 1, wherein said X-ray fluoroscopic means obtains an angiogram by subjecting the fluoroscopic X-ray images obtained after injecting a contrast medium into a blood vessel of the subject to subtraction processing.

4. The apparatus according to claim 1, wherein said X-ray fluoroscopic means includes an image intensifier tube for converting the X-rays which have passed through the subject into the optical image, the optical image output from the image intensifier having a circular view field,
   said display means displays said secondary image outside the circular view field of the fluoroscopic X-ray image, and
   said recording means records the living body data on that part of the fluoroscopic X-ray image data which corresponds to the portion of the main image outside the circular view field of the fluoroscopic X-ray image.

5. The apparatus according to claim 1, wherein said recording means records the fluoroscopic X-ray image data on part of the single image recording area of the recording medium after compressing of the fluoroscopic X-ray image data, and records the living body data on another part of the image recording area of the recording medium.

6. The apparatus according to claim 5, wherein said recording means records the compressed image data following the living body data in the single image recording area of the image recording medium.

7. The apparatus according to claim 5, wherein said recording means records the living body data following the compressed image data in the single image recording area of the image recording medium.

8. The apparatus according to claim 1, further comprising reproducing means for reproducing data from the single image recording area of the recording medium, separating reproduced data into the fluoroscopic X-ray image data and the living body data, and supplying the fluoroscopic X-ray image data and the living body data to said display means.

9. The apparatus according to claim 1, wherein said recording means is a digital video tape recorder.

* * * * *